United States Patent [19]

Hamel et al.

[11] Patent Number: 5,243,057
[45] Date of Patent: Sep. 7, 1993

[54] ENERGETIC AZIDOMETHYL-SUBSTITUTED 1,3-DIOXOLANES

[75] Inventors: Edward E. Hamel, Roseville; Renato R. Rindone, Fair Oaks; Der-Shing Huang, Carmichael, all of Calif.

[73] Assignee: Aerojet-General Corporation, Sacramento, Calif.

[21] Appl. No.: 320,144

[22] Filed: Mar. 7, 1989

[51] Int. Cl.$^5$ ............................................. C07D 317/28
[52] U.S. Cl. .................................. 549/451; 149/109.4
[58] Field of Search ........................................ 549/451

[56] References Cited

U.S. PATENT DOCUMENTS

| | | | |
|---|---|---|---|
| 4,393,199 | 7/1983 | Manser | 528/408 |
| 4,406,718 | 9/1983 | Frankel et al. | 149/96 |
| 4,783,452 | 11/1988 | Haines et al. | 549/451 |

OTHER PUBLICATIONS

J. B. Miller, Jrnl. of Org. Chem., "Diels–Alder Reactions of 4,5-Dimethylenedioxolanes", vol. 25, No. 8, Aug. 8, 1960.
W. S. Anderson et al., 1981 JANNAF Meeting, "Some New Aliphatic Polyazides Derived From Pentaerythritol", vol. 1, May 1981.

Primary Examiner—Nicky Chan
Attorney, Agent, or Firm—Townsend and Townsend Khourie and Crew

[57] ABSTRACT

Methylazide-substituted 1,3-dioxolanes of the generic formula

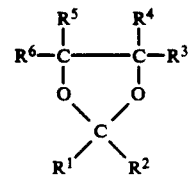

in which $R^1$, $R^2$, $R^3$, $R^4$, $R^5$ and $R^6$ are independently selected from H, $C_1$–$C_6$ alkyl and $CH_2N_3$ are disclosed as energetic plasticizers for rocket and gun propellants and explosives formulations. Methods of preparation of these compounds are also disclosed, in which halogen-substituted vicinal diols are reacted with aldehydes or ketones to form the halo-analog of the product, which is then converted to the product by reaction with a metal azide.

1 Claim, No Drawings

ENERGETIC AZIDOMETHYL-SUBSTITUTED 1,3-DIOXOLANES

BACKGROUND AND SUMMARY OF THE INVENTION

This invention relates to novel chemical compounds used as plasticizers in polymeric formulations. More specifically the invention relates to energetic methylazide-substituted 1,3-dioxolanes and to their use as plasticizers for polymeric binders in rocket and gun propellants and explosive formulations. A process for their preparation is also presented, as well as energetic compositions which include such plasticizers.

Solid double-base propellants such as those used for rocket propellants are prepared by combining a variety of materials consisting of oxidizers, binders, plasticizers and a curing agent to solidify the formulation. The plasticizers may be either energetic or nonenergetic in nature. Energetic plasticizers tend to be somewhat viscous, and this limits the amount of solids that can be included in propellant formulations while maintaining good propellant processibility. Reducing the solids loading of a propellant generally results in a lowered propellant impulse.

This invention relates to a novel class of methylazide-substituted 1,3-dioxolanes for use as plasticizers for propellant systems, many of which are capable of being prepared from readily available starting materials, and to a novel process for their preparation.

This invention also resides in energetic compositions which include the novel class of methylazide-substituted 1,3-dioxolanes as plasticizers. Such compositions have the combined benefits of improved propellant performance due to the energetic nature of the plasticizer, maximized solids loading and ease of processibility of the propellant formulation. The term "energetic compositions" is used herein to include rocket and gun propellant and explosive formulations.

A further object of this invention is to provide a novel method for preparing the energetic dioxolanes from the chloro-substituted 1,3-dioxolanes. The latter compounds are reacted with metal azide to produce the energetic dioxolanes.

DETAILED DESCRIPTION OF THE INVENTION

The novel methylazide-substituted 1,3-dioxolanes of the present invention are represented by the formula:

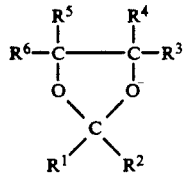

in which $R^1$, $R^2$, $R^3$, $R^4$, $R^5$ and $R^6$ are independently selected from the group consisting of H, $C_1$–$C_6$ alkyl and $CH_2N_3$, such that the total number of azide ($N_3$) groups is at least one, preferably at least two, and most preferably at least three. The term "alkyl" is intended to include both straight- and branched-chain groups. Among the alkyl groups, $C_1$–$C_4$ alkyl are preferred, with $CH_3$ and $CH(CH_3)_2$ particularly preferred. The term "independently selected" is used herein to indicate that two or more of the R groups may be identical.

Examples of 1,3-dioxolanes within the above formula are those in which $R^1$, $R^2$, $R^3$, $R^4$, $R^5$ and $R^6$ are as follows:

| $R^1$ | $R^2$ | $R^3$ | $R^4$ | $R^5$ | $R^6$ |
|---|---|---|---|---|---|
| H | H | $CH_2N_3$ | $CH_2N_3$ | $CH_2N_3$ | $CH_2N_3$ |
| H | H | H | $CH_2N_3$ | H | $CH_2N_3$ |
| $CH_3$ | H | $CH_2N_3$ | $CH_2N_3$ | $CH_2N_3$ | $CH_2N_3$ |
| $CH_3$ | H | H | $CH_2N_3$ | H | $CH_2N_3$ |
| $CH_2N_3$ | H | $CH_2N_3$ | $CH_2N_3$ | $CH_2N_3$ | $CH_2N_3$ |
| $CH_2N_3$ | H | H | $CH_2N_3$ | H | $CH_2N_3$ |
| $CH(CH_3)_2$ | H | $CH_2N_3$ | $CH_2N_3$ | $CH_2N_3$ | $CH_2N_3$ |
| $CH(CH_3)_2$ | H | H | $CH_2N_3$ | H | $CH_2N_3$ |
| H | H | H | H | H | $CH_2N_3$ |
| $CH_3$ | H | H | H | H | $CH_2N_3$ |
| $CH_2N_3$ | H | H | H | H | $CH_2N_3$ |
| $CH(CH_3)_2$ | H | H | H | H | $CH_2N_3$ |
| H | H | H | H | $CH_2N_3$ | $CH_2N_3$ |
| $CH_3$ | H | H | H | $CH_2N_3$ | $CH_2N_3$ |
| $CH_2N_3$ | H | H | H | $CH_2N_3$ | $CH_2N_3$ |
| $CH(CH_3)_2$ | H | H | H | $CH_2N_3$ | $CH_2N_3$ |
| $CH_3$ | $CH_3$ | $CH_2N_3$ | $CH_2N_3$ | $CH_2N_3$ | $CH_2N_3$ |
| $CH_3$ | $CH_3$ | H | $CH_2N_3$ | H | $CH_2N_3$ |
| $CH_3$ | $CH_3$ | H | H | H | $CH_2N_3$ |
| $CH_3$ | $CH_3$ | H | H | $CH_2N_3$ | $CH_2N_3$ |
| $CH_3$ | $CH_3$ | H | H | $CH_2N_3$ | $CH_3$ |
| $CH_2N_3$ | $CH_2N_3$ | $CH_2N_3$ | $CH_2N_3$ | $CH_2N_3$ | $CH_2N_3$ |
| $CH_2N_3$ | $CH_2N_3$ | H | $CH_2N_3$ | H | $CH_2N_3$ |
| $CH_2N_3$ | $CH_2N_3$ | H | H | H | $CH_2N_3$ |
| $CH_2N_3$ | $CH_2N_3$ | H | H | $CH_2N_3$ | $CH_2N_3$ |

Within the scope of the above formula, certain embodiments are preferred, namely those in which $R^1$, $R^2$, $R^3$, $R^4$, $R^5$ and $R^6$ are independently selected from the group H, $CH_3$, $CH(CH_3)_2$ and $CH_3N_3$, such that the total number of azide ($N_3$) groups is two or three, compounds in which $R^3$ and $R^5$ are $CH_2N_3$, and compounds in which $R^1$, $R^2$, $R^3$, $R^4$, $R^5$ and $R^6$ are $CH_2N_3$, and compounds in which $R^1$ and $R^2$ are alkyl groups other than methyl.

The 1,3-dioxolanes of the present invention may be prepared, broadly speaking, by reacting, in the presence of a condensation catalyst such as concentrated sulfuric acid, halomethyl-substituted vicinal diol with a compound having either an aldehyde or a ketone functionality. This latter compound is then reacted with metal azide in an aprotic solvent to give the corresponding azide plasticizers. Acetaldehyde, chloroacetaldehyde, isobutyraldehyde and 1,3,5-trioxane are well known in the art as suppliers of the aldehyde functionality. Acetone and 1,3-dichloroacetone are also well known as suppliers of the ketone functionality. Reactions of the alcohols with either the aldehyde or the ketone compounds preferably take place at −25° C. to 35° C. in a heterogeneous mixture, low boiling solvent, and condensation catalyst, with yields ranging to the high 90's in percent. Particularly preferable are reactions taking place at −15° C. to 30° C., with dichloroethane as solvent and an acid catalyst, with yields ranging from 85 to 99.9 weight percent. The second step, reacting the halo-substituted 1,3-dioxolane of the first step with metal azide, preferably takes place at 70° C. to 120° C., with yields ranging from 50 to 99 weight percent. This reaction is particularly preferable with sodium azide at 70° C. to 100° C., with dimethyl sulfoxide as solvent. Yields of about 85 to 99.9 percent are particularly preferable.

The following examples are intended to illustrate the invention and are in no way to be considered as limitations on the inventive concept.

EXAMPLE 1

1. Preparation of 4,5-Dichloromethyl-1,3-dioxolane

A three-neck 500-mL flask equipped with a thermometer, a mechanical stirrer, an addition funnel, a condenser, and a positive nitrogen atmosphere was charged with 1,4-dichloro-2,3-butanediol (50.0 g, 0.314 mole), trioxane (9.43 g, 0.314 mole), and 1,2-dichloroethane (EDC) (300 mL). The 1,4-dichloro-2,3-butanediol was not totally dissolved. Concentrated sulfuric acid (46.3 g, 0.455 mole) was then added dropwise over eight minutes. During the addition period, a slight exotherm was noticed and the flask was immersed in an ice bath to maintain the reaction temperature at 21.5° C. to 25.5° C. for 2.1 hours. The reaction mixture was permitted to settle overnight. The acid layer was removed, washed once with 30 mL EDC, and discarded. The combined EDC solutions were quenched with 2% NaHCO$_3$ (600 mL), washed with deionized water (400 mL), 1% NaHCO$_3$ solution (400 mL), deionized water (400 mL, twice), and stripped in vacuo. The resulting light yellow liquid weighed 48.9 g (89.5% yield), and contained 1.8% EDC and 98.2% dl- and meso-(4,5-dichloromethyl)-1,3-dioxolane, as determined by GC analysis and proton NMR (CDCl$_3$) δ (s, —OCH$_2$O—), 4.1 (m, ClCH$_2$CHCHCH$_2$Cl), 3.6(d, ClCH$_2$C$\underline{H}$CHCH$_2$Cl).

2. Preparation of 4,5-Diazidomethyl-1,3-dioxolane

In this compound, R$^3$ and R$^6$ are both CH$_2$N$_3$, and the remaining R-groups are all H.

A three-neck 250-mL flask equipped with a mechanical stirrer, a thermometer, an addition funnel, a thermowatch, a heating mantle, a condenser, and a positive nitrogen atmosphere was charged with 75 mL of dimethyl sulfoxide (DMSO) and heated to 75° C. to 80° C. Sodium azide (4.0 g, 61.5 mmoles) was then added in one portion. The mixture was heated to 90° C. A solution of 4,5-(dichloromethyl)-1,3-dioxolane (5.0 g, 29.0 mmoles) in 50 mL DMSO was then prepared and added dropwise to the sodium azide/DMSO mixture over 27 minutes at 90.0° C. to 90.8° C. Stirring was continued for 12.6 hours at 90° C. to 97° C. following the addition. The mixture was then chilled to ambient temperature, quenched with deionized water (750 mL), and extracted twice with methylene chloride (100 mL). The aqueous solution (923.7 g) was discarded. The methylene chloride solution was washed with deionized water (300 mL) six times, and stripped in vacuo to give a yellow liquid weighing 5.19 g (97.2% yield); identified as 4,5-diazidomethyl-1,3-dioxolane by infrared spectroscopy (film): 2900 cm$^{-1}$ (CH), 2100 cm$^{-1}$ (N$_3$), 1285 cm$^{-1}$, 1165 cm$^{-1}$, 1095 cm$^{-1}$(—OCH$_2$O—); proton NMR (CDCl$_3$) δ 5.05 (s, OCH$_2$O), 3.9 (m, N$_3$CH$_2$C$\underline{H}$CHCH$_2$N$_3$), 3.45 (d, N$_3$C$\underline{H}_2$CHCHC$\underline{H}_2$N$_3$).

EXAMPLE 2

1. Preparation of 2,4,5-Trichloromethyl-1,3-dioxolane

A 2-liter three-neck jacketed flask fitted with a mechanical stirrer, a digital thermoprobe, an addition funnel, a condenser, and a positive nitrogen atmosphere was charged with 1,4-dichloro-2,3-butanediol (DCBD) (200.0 g, 1.256 mole) and 1,2-dichloroethane (EDC) (1000 mL). The mixture was stirred at ambient temperature for a few minutes and chloroacetaldehyde in water (50–55%, 196.8 g) was added in one portion. A slight endotherm was noticed, and the DCBD was not totally dissolved. The mixture was then chilled to −15° C. and concentrated sulfuric acid (96.4%, 489.6 g) was added dropwise over 1.8 hours at −8° C. to −15.6° C. After the completion of the sulfuric acid addition, the resulting reddish pink reaction mixture was warmed to ambient temperature and permitted to stand overnight, during which time the color of the reaction mixture turned to dark brown. The bottom acid layer was then removed and washed with 200 mL EDC. The combined EDC layers were then washed with 2% NaHCO3 solution (500 mL, twice), followed by deionized water 500 mL, three times). A rag phase was separated out, weighing 82.2 grams and containing mainly EDC. After washing, the EDC layer was stripped in vacuo to give a dark brown liquid weighing 238.8 g (86.6% yield), identified as 2,4,5-trichloromethyl-1,3-dioxolane by proton NMR (CDCl$_3$): 5.4 (t, ClCH$_2$CHO), 4.32 (m, ClCH$_2$CH(—CH)—O), 3.73, 3.67 (d, ClC$\underline{H}_2$CH(—CH)—O), 3.60, 3.56 (d,ClCH$_2$CH(—O)—O). GC analysis indicated that the purity of the product was 99.0 area percent.

2. Preparation of 2,4,5-Triazidomethyl-1,3-dioxolane

In this compound, R$^1$ is CH$_2$N$_3$, R$^3$ and R$^6$ are both CH$_2$N$_3$, and the remaining R-groups are all H.

A 2-liter four-neck flask fitted with a condenser, a mechanical stirrer, a thermometer, a thermowatch, a heating mantle, an addition funnel and a positive nitrogen atmosphere was charged with 500 mL of dimethyl sulfoxide (DMSO) and heated to 77° C. Sodium azide (222.7 g, 3.43 moles) was added in one portion and the slurry was heated to 95° C. To the slurry was then added 2,4,5-trichloromethyl-1,3-dioxolane (238.7 g, 1.09 moles) in 300 mL DMSO solution in dropwise over 1.1 hour at 93° C. to 99.5° C. Heating was continued following the addition 13.1 hours at 93.5° C. to 98° C. During this period, four samples were taken to monitor the disappearance of the starting material. After cooling overnight, the resulting dark brown reaction mixture was filtered by an internal filter and the filtrate was placed in a 5-liter flask which was fitted with a mechanical stirrer, a thermometer, and a vacuum trap. The filtrate was quenched with 2000 mL of deionized water and 200 mL of methylene chloride. After phase separation the aqueous phase was extracted four times with 500 mL of methylene chloride. The resulting aqueous layer was discarded. The combined methylene chloride phases were washed eight times with 1000 mL of deionized water, dried over 100 g of anhydrous sodium sulfate, and purified by a silica gel column. After purification, the combined methylene chloride phaes weighed 3291.5 g.

A small portion of this solution was stripped in vacuo to give a light yellow liquid. Total chloride analysis indicated that the solution contained 11.0 weight percent chloride which is equivalent to 77.3 percent conversion. Due to its high chloride content, the solution was stripped in vacuo and recycled. The unconverted starting material (238.6 g) in 300 mL DMSO was treated with sodium azide (89.1 g) in 400 mL DMSO for 21.2 hours at 93° C. to 99.5° C. The workup procedures described above were repeated, followed by purification on a silica gel column. The purified product solution weighed 3720.9 g (221.3 g product, 85.1% yield). A small portion of this solution (144.95 g) was stripped in vacuo to give a light yellow liquid (8.62 g). Total chloride analysis indicated that the product contained 0.6 weight percent chloride which is equivalent to 98.8% chloride conversion. The product had a density (at 25°

C.) of 1.40 g/mL, a freezing point of less than −16° C., and a purity (by GC) of 94.4%. The structure of the product was confirmed as that of 2,4,5-triazidomethyl-1,3-dioxolane by proton NMR (CDCl3): δ 5.28 (t, N3CH2CHO—), 4.10 (m, N3CH2CHCHCH2N3), 3.65 (d, N3CH2CHCHCH2N3), 3.47 (d, N3CH2CHO—); FTIR (film), 2930 cm$^{-1}$ (CH), 2104 cm$^{-1}$ (N3), 1284 cm$^{-1}$, 1143 cm$^{-1}$, 1076 cm$^{-1}$ (OCHO).

EXAMPLE 3

Preparation of 2-Isopropyl-4,5-dichloromethyl-1,3-dioxolane

A three-neck 5-mL flask fitted with a thermometer, mechanical stirrer, addition funnel, condenser and positive nitrogen atmosphere was charged with EDC (200 mL), isobutyraldehyde (11.3 g, 0.157 mole), and 1,4-dichloro-2,3-butanediol (25.0 g, 0.157 mole). Concentrated sulfuric acid (23.2 g) was added dropwise to the agitated mixture over thirty minutes, during which time a slight exotherm was noticed and the flask was immersed in an ice bath to maintain a reaction temperature of 17°–19° C. Stirring was then continued at ambient temperature (20° C.) for five hours.

For product recovery, the lower acid layer was extracted with 90 mL EDC and discarded. The EDC layer and the EDC extract were combined, washed with two 100-mL portions of 1% NaHCO3 solution, two 300-mL portions of deionized water, and stripped in vacuo. The resulting light yellow liquid weighed 25.71 g (76.9% yield), and was identified as 2-isopropyl-4,5-dichloromethyl-1,3-dioxolane by proton NMR (CDCl3): δ 4.9 (d, —OCHO—), 4.2 (m, —CHCH—), 3.7 (d, two —CH2Cl), 1.8 (m, (CH3)2CHCH—), 1.0 (d, (CH3)2CHCH—); and infrared spectroscopy (film): 2877–2965 cm$^{-1}$ (C—H stretch), 1100 cm$^{-1}$ (C—O—C stretch), 759 cm$^{-1}$ (C—Cl stretch).

2. Preparation of 2-Isopropyl-4,5-diazidomethyl-1,3-dioxolane

In this compound, R$^1$ is CH(CH3)2, R$^3$ and R$^6$ are both CH2N3, and the remaining R-groups are all H.

A three-neck 250-mL flask fitted with a mechanical stirrer, thermometer, thermo-watch, heating mantle, condenser, addition funnel, and a positive nitrogen atmosphere was charged with DMSO (100 mL) and heated to 80° C. Sodium azide (15.87 g, 0.244 mole) was then added in one portion. The mixture was heated to 94.5° C. The product of part 1 of this example (24.65 g, 0.116 mole) was dissolved in 50 mL DMSO, and the resulting solution added dropwise to the sodium azide/DMSO mixture over thirty minutes at 91°–97° C. Once the addition was complete, stirring was continued for an additional 24.1 hours at 93.5°–99° C.

The mixture was then chilled to ambient temperature, quenched with 700 mL of deionized water, and then extracted with four 100-mL portions of methylene chloride. The aqueous layer was discarded. The combined extracts were washed with seven 400-mL portions of deionized water, dried over anhydrous sodium sulfate (50 g), and purified by a silica gel column. The resulting solution was stripped in vacuo to give a yellow liquid weighing 24.23 g (92.3% yield). The latter was identified as 2-isopropyl-4,5-diazidomethyl-1,3-dioxolane by infrared spectroscopy (film) 2878–2967 cm$^{-1}$ (C—H stretch), 2104 cm$^{-1}$ (N3), 1282 cm$^{-1}$ (asymmetric C—O—C stretch), 1195 cm$^{-1}$ (symmetric C—O—C stretch); proton NMR (CDCl3): δ 4.8 (d, —OCHO—), 3.9 (m, —CHCH—), 3.4 (d, two —CHCl), 1.8 (m, (CH3)2CHCH—), 0.9 (d, (CH3)2CHCH—).

Table 1 presents presents calculated thermodynamic properties for 2,4,5-triazidomethyl-1,3-dioxolane (Compound A), 4,5-diazidomethyl-1,3-dioxolane (Compound B) and 2-isopropyl-4,5-diazidomethyl-1,3-dioxolane (Compound C). Table 2 lists experimentally derived hazard properties for the same three compounds using industry standard test procedures. These tests included a differential thermal analysis (DTA), a Bureau of Mines impact test (using a 2-kg weight), a rotary friction test and an electric spark sentivity test.

TABLE 1

CALCULATED THERMODYNAMIC PROPERTIES

| | Compounds: | | |
|---|---|---|---|
| | A | B | C |
| Heat of formation (kcal/mole) | +168.2 | +79.9 | +52.2 |
| Heat of combustion (kcal/mole) | −1040.2 | −823.6 | −1283.1 |

TABLE 2

HAZARD PROPERTIES

| | Compounds: | | |
|---|---|---|---|
| | A | B | C |
| Impact (cm/2 kg) | 34 | >100 | >100 |
| DTA (°C.) | | | |
| exotherm onset | 172.8 | 154 | 176 |
| exotherm peak | 238.0 | 210 | 227 |
| Rotary friction (g/2000 rpm) | 1300 | >4000 | >4000 |
| Spark sensitivity (joules) | >1.0 | >1.0 | >1.0 |

To those skilled in the art, it will be readily apparent that many modifications and variations of the present invention are possible in light of the above teachings. It is therefore to be understood that the present invention may be practiced otherwise than as specifically described herein and still be within the spirit and scope of the appended claims.

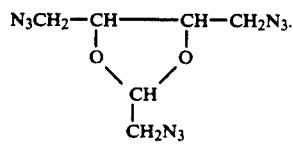

What is claimed is:

1. A compound having the formula